United States Patent [19]

Fuchs et al.

[11] 4,154,729

[45] May 15, 1979

[54] CONTINUOUS EXTRACTION OF CAPROLACTAM FROM CRUDE LACTAM

[75] Inventors: Hugo Fuchs, Ludwigshafen; Uwe Brand, Rosengarten; Klaus Kartte, Beindersheim, all of Fed. Rep. of Germany

[73] Assignee: BASF Aktiengesellschaft, Fed. Rep. of Germany

[21] Appl. No.: 848,210

[22] Filed: Nov. 3, 1977

[30] Foreign Application Priority Data

Dec. 11, 1976 [DE] Fed. Rep. of Germany ....... 2656182

[51] Int. Cl.$^2$ .......................................... C07D 201/16
[52] U.S. Cl. .............................................. 260/239.3 A
[58] Field of Search ................................. 260/239.3 A

[56] References Cited

U.S. PATENT DOCUMENTS

| | | | |
|---|---|---|---|
| 2,758,991 | 8/1956 | Kretzers et al. | 260/239.3 A |
| 3,761,467 | 9/1973 | Williams et al. | 260/239.3 A |
| 3,852,272 | 12/1974 | De Rooij | 260/239.3 A |
| 3,852,273 | 12/1974 | De Rooij | 260/239.3 A |
| 4,036,830 | 7/1977 | De Rooij et al. | 260/239.3 A |

*Primary Examiner*—Natalie Trousof
*Assistant Examiner*—Robert T. Bond
*Attorney, Agent, or Firm*—Keil & Witherspoon

[57] ABSTRACT

In a process for the continuous extraction of caprolactam from crude lactam by means of benzene in countercurrent, in which crude lactam is fed into the upper part of an extraction zone and benzene into the lower part, a solution of caprolactam in benzene is taken off at the top and an aqueous solution containing impurities is taken off at the bottom, the improvement that water is additionally fed into the upper part of the extraction zone and a part of the aqueous solution, containing impurities, obtained at the bottom of the extraction zone is recycled into the extraction zone. Caprolactam is used for the manufacture of nylon.

7 Claims, 1 Drawing Figure

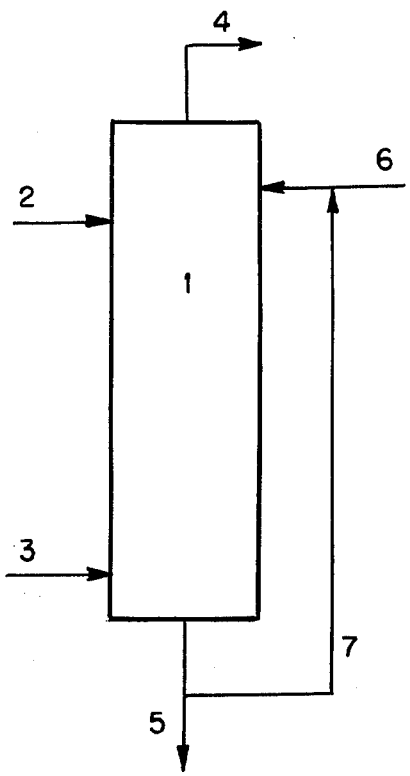
LEGENDS
1. COUNTERCURRENT COLUMN
2. CRUDE CAPROLACTAM FEED
3. BENZENE
4. SOLUTION OF CAPROLACTAM IN BENZENE
5. AQUEOUS SOLUTION CONTAINING IMPURITIES
6. FRESH WATER
7. RECYCLED AQUEOUS SOLUTION CONTAINING IMPURITIES

CONTINUOUS EXTRACTION OF CAPROLACTAM FROM CRUDE LACTAM

The present invention relates to a process for the continuous extraction of caprolactam from crude lactam by means of benzene in counter-current, in which crude lactam is fed into the upper part of an extraction zone and benzene into the lower part, a solution of caprolactam in benzene is taken off at the top and an aqueous solution containing impurities is taken off at the bottom.

The direct extraction of caprolactam from the neutralized reaction mixture of the Beckmann rearrangement with benzene is disclosed in German Published Application DAS No. 1,031,308. However, in order to extract all the caprolactam, the extraction must be carried out in two stages. Apart from the fact that large amounts of aqueous solutions have to be extracted, there is the fact that the impurities remain in the aqueous ammonium sulfate solution, making the isolation of pure ammonium sulfate more difficult. For this reason, the caprolactam which separates out as the oily phase from the neutralized mixture of the Beckmann rearrangement is separated off as crude lactam and extracted with benzene. As described in German Patent No. 930,447, the crude lactam should be concentrated, before the extraction, to a content of from 80 to 90% by weight of caprolactam. Because of the impurities, such as aminoacids and sulfonated products, contained in the crude lactam, satisfactory phase separation of the benzene extract solution and the aqueous phase cannot be relied on. Even if, as in German Patent No. 1,194,863, crude lactam as separated off is extracted with benzene, difficulties in phase separation arise. In addition, some proportion of caprolactam is always discharged with the aqueous solution as effluent and is therefore lost. In view of the need to keep waters unpolluted, such effluent cannot be discharged without subjecting it to an expensive treatment.

It is an object of the present invention to carry out the extraction of caprolactam from crude caprolactam in such a way that no difficulties in phase separation occur, that the water discharged contains very little caprolactam and that, on the other hand, this water is produced in limited amount, with such a high content of impurities that it can be disposed of by combustion.

We have found that this object is achieved and that the continuous extraction of caprolactam from crude lactam by means of benzene in counter-current, in which crude lactam is fed into the upper part of an extraction zone and benzene into the lower part, a solution of caprolactam in benzene is taken off at the top and an aqueous solution containing impurities is taken off at the bottom, can be carried out more advantageously than hitherto if water is additionally fed into the upper part of the extraction zone and a part of the aqueous solution, containing impurities, obtained at the bottom of the extraction zone is recycled into the extraction zone.

The new process has the advantage that only a limited amount of effluent is formed and that this has such a high content of impurities that it can be disposed of by combustion. In addition, the amount of caprolactam discharged with the effluent is reduced. Furthermore, the extraction is troublefree and gives good phase separation.

It was not obvious to recycle a part of the aqueous solution obtained, containing impurities, into the extraction zone since the impurities, such as sulfonated products, would have been expected to give difficulties in phase separation.

The invention is described in conjunction with the accompanying drawing which represents a schematic flow diagram of the present process.

In the drawing, crude caprolactam is fed through line 2 to the upper part of a countercurrent extraction column 1 and benzene is fed to the lower part of the column through line 3. Water is additionally fed to the upper part of column 1 through line 6. A solution of caprolactam in benzene is taken off at the top of column 1 through line 4 while an aqueous solution containing impurities is taken off at the bottom through line 5. A portion of the aqueous solution containing impurities is recycled through line 7.

According to the invention, crude lactam as obtained by separation from the neutralized reaction mixture of the Beckmann rearrangement is used as the starting material. A suitable process is described, for example, in German Patent No. 1,194,863. The crude lactam contains, for example, about 70% of caprolactam and 30% of an aqueous solution containing ammonium sulfate. The mixture further contains impurities, eg. aminocarboxylic acids, sulfonated products and other, unidentified, compounds.

The crude lactam is extracted with benzene in counter-current in an extraction zone, the method used being that crude lactam is fed into the upper part of the extraction zone and benzene into the lower part, a solution of caprolactam in benzene is taken off at the top and an aqueous solution containing impurities is taken off at the bottom. As a rule, the amount by weight of benzene is from 2 to 12, especially from 2.5 to 10, times the amount by weight of crude lactam. The extraction is carried out at, for example, from 40° to 60° C., as a rule under atmospheric pressure or slightly superatmospheric pressure, eg. at up to 1.5 bars.

An essential characteristic of the invention is that water is additionally fed into the upper part of the extraction zone and at the same time a part of the aqueous solution, containing impurities, obtained at the bottom of the extraction zone is recycled. Advantageously, from 17 to 25 parts by weight of water, in the form of fresh water plus aqueous solution containing impurities, are fed in per 100 parts by weight of crude lactam. Of the total amount of water added (fresh water + aqueous solution containing impurities), advantageously from 20 to 75% are fresh water and from 25 to 80% are in the form of recycled aqueous solution containing impurities. This corresponds to from 0.09 to 0.36 times the total amount of aqueous solution, containing impurities, which is formed.

Advantageously, crude lactam is introduced into the upper one-fifth of the extraction zone and benzene into the lower one-fifth, whilst the additional amount of water is fed in above the crude lactam feed point and below the point at which the solution of caprolactam in benzene is taken off. The recycled aqueous solution, containing impurities, is generally added together with the fresh water. However, it has proved particularly advantageous if the recycled aqueous solution is fed into the extraction zone together with the crude lactam.

Conventional extraction columns, for example perforated tray columns or packed columns, may be used for the extraction. Suitable perforated tray columns have, for example, from 20 to 60 perforated trays, above which there are from 4 to 10 wash trays. The crude lactam, if appropriate together with the recycled aqueous solution, is advantageously fed on to the uppermost perforated tray, whilst the fresh water is fed onto the uppermost wash tray. Benzene is advantageously fed in between the first and the third perforated tray. The solution of caprolactam in benzene is taken off at the top of the column whilst the aqueous solution containing impurities is discharged at the bottom of the column.

The resulting solution of caprolactam in benzene, which contains, for example, from 6 to 20 percent by weight of caprolactam, is worked up by distillation and the caprolactam is separated off as described, for example, in German Patent No. 1,194,863.

The aqueous solution obtained contains impurities in a concentration of, for example, from 5 to 25 percent by weight; apart from these, only up to 0.2 percent by weight of caprolactam is present. Such an aqueous solution can be disposed of by combustion, without great expense.

Caprolactam is used for the manufacture of nylon-6.

The Examples which follow illustrate the process of the invention.

EXAMPLE 1

Per hour, 1,000 parts by weight of an aqueous crude lactam solution of about 70% strength by weight are fed onto the 30th tray of an extraction column with 35 perforated trays. At the same time, about 2,800 parts by weight of benzene are fed in between the 1st and 2nd trays. The extraction temperature is 55° C. A total of 180 parts by weight of water is charged onto the 34th tray to wash the benzene-lactam solution formed. This water is composed of 40 parts by weight of water and 140 parts by weight of waste water from the extraction. In the lower part of the column, 300 parts by weight of waste water, which on evaporation leave about 30 parts by weight of residue, are obtained per hour. The waste water still contains about 0.1% of lactam. At the top of the column, 3,540 parts by weight of a benzene-lactam solution are obtained per hour, the solution containing 699.7 parts by weight of lactam, 40.3 parts by weight of water and 2,800 parts by weight of benzene.

The resulting lactam, freed from benzene, has a permanganate number of 60 and can subsequently be purified by distillation.

The permanganate number of caprolactam is determined by a photometric method.

The extinction at a wavelength of 420 nm is measured from the light transmission of a 1% strength caprolactam solution in water (100 ml) with the addition of 2 ml of 0.01 - normal $KMnO_4$ solution at 25° C. after 600 seconds, against an identical solution without caprolactam. The 100-fold value of the extinction is quoted as the permanganate absorption number (see Ullmanns Encyclopädie der techn. Chemie, 4th edition, volume 9, page 110).

COMPARATIVE EXAMPLE

The procedure followed is as described in Example 1. However, the water for washing is made up only of fresh water. 440 parts by weight of waste water, which on evaporation leave about 30 parts by weight of residue, are then obtained per hour. This waste water contains about 0.2% of lactam.

EXAMPLE 2

Per hour, 1,000 parts by weight of a 70% strength aqueous crude lactam solution are fed onto the 30th tray of the extraction column described in Example 1. At the same time, about 2,800 parts by weight of benzene are fed in between the 1st and 2nd trays. The extraction temperature is about 55° C. On the 34th tray, 40 parts by weight of fresh water are fed in, for the purpose of washing the benzene-lactam solution formed. At the same time, 140 parts by weight of waste water (leaving a residue of 14 parts by weight on evaporation) are taken, per hour, off the column bottom and added to the crude lactam. Per hour, 3,540 parts by weight of a benzene-lactam solution are obtained from the upper part of the column; the benzene is removed from this solution by distillation. The caprolactam obtained has a permanganate absorption number of 45 and can subsequently be purified by distillation.

We claim:

1. In a process for the continuous extraction of caprolactam from crude lactam by means of benzene in counter-current, in which crude lactam is fed into the upper part of an extraction zone and benzene into the lower part, a solution of caprolactam in benzene is taken off at the top and an aqueous solution containing impurities is taken off at the bottom, wherein the improvement comprises: additionally feeding water into the upper part of the extraction zone and recycling a part of the aqueous solution, conntaining impurities, obtained at the bottom of the extraction zone into the extraction zone.

2. A process as set forth in claim 1, in which a total of from 17 to 25 parts by weight of water are additionally fed in per 100 parts by weight of crude lactam.

3. A process as set forth in claim 1, in which from 0.09 to 0.36 times the amount of aqueous solution, containing impurities, obtained at the bottom of the extraction zone is recycled.

4. A process as set forth in claim 1, in which the additional water fed in, and the recycled part of the aqueous solution containing impurities, are fed into the extraction zone above the feed point of the crude lactam.

5. A process as set forth in claim 1, in which the recycled amount of aqueous solution containing impurities is fed into the extraction zone together with the crude lactam.

6. A process as set forth in claim 1, in which the extraction is carried out at from 40° to 60° C.

7. A process as set forth in claim 1, in which the amount by weight of benzene used is from 2 to 12 times the amount by weight of crude lactam.

* * * * *